(12) United States Patent
Lowery

(10) Patent No.: US 7,937,987 B2
(45) Date of Patent: May 10, 2011

(54) FILTER MONITOR-FLOW METER COMBINATION SENSOR

(75) Inventor: Patrick A. Lowery, Greer, SC (US)

(73) Assignee: Circor Instrumentation Technologies, Inc., Spartanburg, SC (US)

( * ) Notice: Subject to any disclaimer, the term of this patent is extended or adjusted under 35 U.S.C. 154(b) by 847 days.

(21) Appl. No.: 11/864,133

(22) Filed: Sep. 28, 2007

(65) Prior Publication Data

US 2009/0084164 A1    Apr. 2, 2009

(51) Int. Cl.
    *G01N 15/08* (2006.01)
(52) U.S. Cl. .......................................................... 73/38
(58) Field of Classification Search ................... 73/38
    See application file for complete search history.

(56) References Cited

U.S. PATENT DOCUMENTS

| | | | |
|---|---|---|---|
| 1,735,789 A | 11/1929 | Powell | |
| 3,754,398 A | 8/1973 | Mattavi | |
| 3,921,754 A | 11/1975 | Hess | |
| 3,970,439 A | 7/1976 | Murphy | |
| 4,128,004 A * | 12/1978 | Caron et al. ........................ | 73/38 |
| 4,704,145 A | 11/1987 | Norris et al. | |
| 4,825,652 A | 5/1989 | Curran | |
| 5,215,560 A | 6/1993 | Lee | |
| 512,681 A | 1/1994 | Clute | |
| 5,427,610 A | 6/1995 | Croker | |
| 5,713,970 A | 2/1998 | Raring | |
| 5,819,683 A | 10/1998 | Ikeda et al. | |
| 5,865,205 A | 2/1999 | Wilmer | |
| 5,900,043 A * | 5/1999 | Grandjean et al. ............... | 95/29 |
| 6,119,710 A | 9/2000 | Brown | |
| 6,152,162 A | 11/2000 | Balazy | |
| 6,334,959 B1 * | 1/2002 | Sutton et al. .................. | 210/767 |
| 6,428,609 B1 | 8/2002 | Moore et al. | |
| 6,453,257 B1 | 9/2002 | Juhasz | |
| 6,547,844 B2 | 4/2003 | Rikyuu et al. | |
| 6,568,282 B1 * | 5/2003 | Ganzi ........................ | 73/861.42 |
| 6,936,085 B2 | 8/2005 | DeMarco | |
| 2002/0196153 A1 | 12/2002 | Kinugawa et al. | |
| 2005/0198944 A1 | 9/2005 | Saitoh et al. | |
| 2007/0172962 A1 | 7/2007 | Sehgal et al. | |

FOREIGN PATENT DOCUMENTS

| | | |
|---|---|---|
| DE | 39 17 856 A1 | 12/1989 |
| EP | 0 592 066 A1 | 4/1994 |
| JP | 55086519 A | 6/1980 |
| JP | 07159307 | 6/1995 |
| JP | 10328647 A | 12/1998 |
| WO | 2005017415 A1 | 2/2005 |

* cited by examiner

*Primary Examiner* — Hezron Williams
*Assistant Examiner* — Nathaniel Kolb
(74) *Attorney, Agent, or Firm* — McNees Wallace & Nurick LLC

(57) ABSTRACT

A method for monitoring a filter installed in a fluid system. The steps include providing a reference region in the fluid system, the region including a chamber having a known volume and releasing a fluid from the chamber configured to flow through the reference region. The method further includes measuring pressure and temperature values at predetermined locations at predetermined time intervals and determining filter permeability values in response to measured pressure and temperature values. The method further includes comparing the filter permeability values to predetermined filter permeability values.

11 Claims, 5 Drawing Sheets

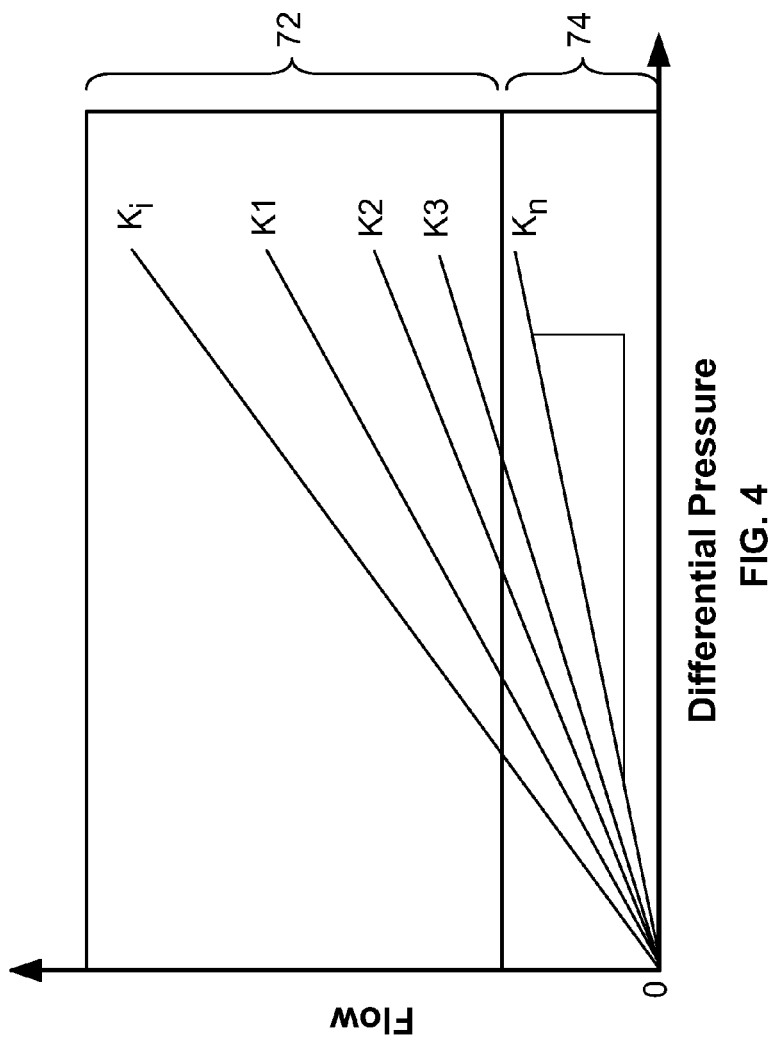
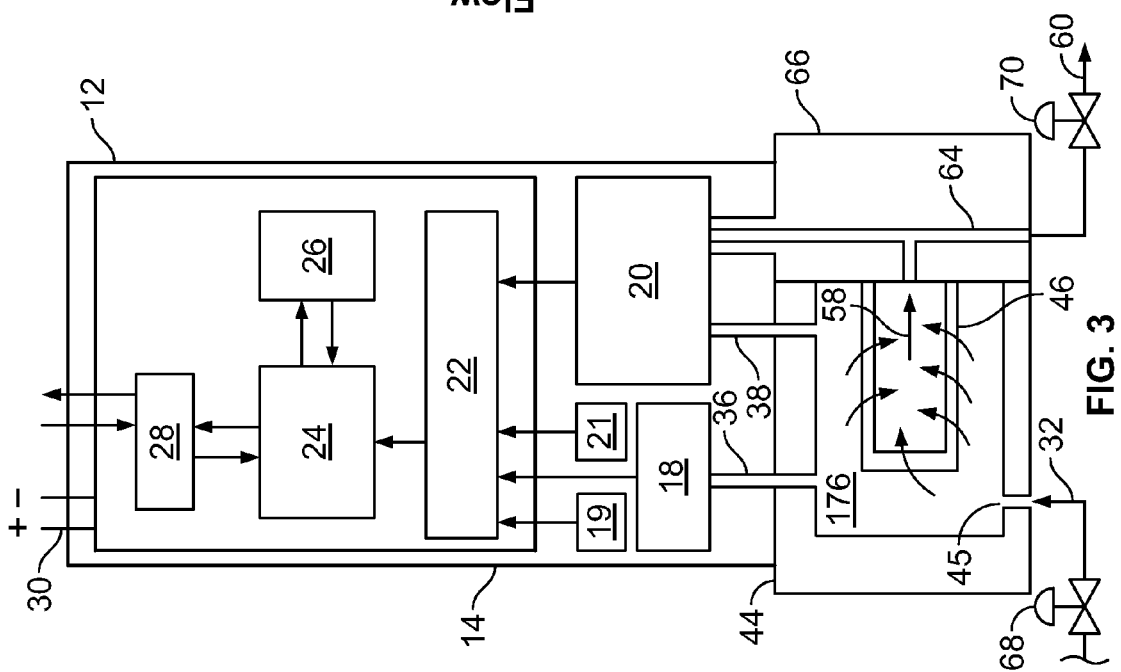

FILTER MONITOR-FLOW METER COMBINATION SENSOR

CROSS-REFERENCE TO RELATED APPLICATIONS

This Application is related to application Ser. No. 11/863,988, filed contemporaneously with this Application on Sep. 28, 2007, entitled "NON-CLOGGING FLOW RESTRICTION FOR PRESSURE BASED FLOW CONTROL DEVICES" assigned to the assignee of the present invention and which is incorporated herein by reference in its entirety.

FIELD OF THE INVENTION

The present invention relates generally to fluid flow systems and, more particularly, to monitoring performance of components of fluid flow systems.

BACKGROUND OF THE INVENTION

Many industrial applications require monitoring of fluid flows. In addition, the fluid flow streams may contain contaminants, such as particulate matter that may be removed from the flow streams by filtration. Over time, filters can clog, often requiring shut-down of plant critical analyzer equipment in order to replace the filters.

Thus, there is a need for determining when filter replacement is required, and further, a framework for predicting when tests for determining possible filter replacement should be conducted.

SUMMARY OF THE INVENTION

For laminar or porous flow through a permeable membrane or porous element such as a filter, the flow is governed by Darcy's law as shown for Equation 1.

$$\dot{Q} = \frac{dV}{dt} = \kappa \frac{\pi d^2 \Delta P}{4 \eta L} \quad [1]$$

Equation 2 shows the circumstance when a first pressure gauge (P1) and a differential pressure sensor (ΔP) are employed in the Darcy's law equation, while Equation 3 represents shows the circumstance when first and second pressure gauges (P1, P2) or absolute pressure sensors are employed in the Darcy's law equation.

$$\dot{Q} = \frac{dV}{dt} = \kappa \frac{\pi d^2 (\Delta P)}{4 \eta L} \quad [2]$$

$$\dot{Q} = \frac{dV}{dt} = \kappa \frac{\pi d^2 (P_1 - P_2)}{4 \eta L} \quad [3]$$

By substitution of fluid density (ρ) as shown in Equation 4 from the ideal gas law equation having non-ideal compressibility, Equations 5 and 6 (for liquid flows) are obtained.

$$\rho = \frac{P}{RTZ(P,T)} \quad [4]$$

$$\dot{m} = \frac{dm}{dt} = \rho \dot{Q} = \kappa \frac{\pi d^2 M_w \Delta P P_1}{4 \eta L R T Z(P,T)} \quad [5]$$

$$\dot{m} = \frac{dm}{dt} = \rho \dot{Q} = \rho \kappa \frac{\pi d^2 (P_1 - P_2)}{4 \eta L} \quad [6]$$

Filter permeability (κ) can then be calculated as shown in Equation 7 (using volumetric flow) and Equation 8 (using mass flow for gases).

$$\kappa = \frac{4 \eta L \dot{Q}}{\pi d^2 \Delta P} = \frac{4 \eta L}{\pi d^2 \Delta P}\left(\frac{dV}{dt}\right) \quad [7]$$

$$\kappa = \frac{4 \eta L \dot{m}}{\pi d^2 \Delta P} = \frac{4 \eta L R T Z(P,T)}{\pi d^2 M_w \Delta P P_1}\left(\frac{dm}{dt}\right) \quad [8]$$

Once filter permeability is known from an initial state calculation of mass flow or volumetric flow (by measuring pressure drop over time in a fixed volume), the fluid viscosity (η) can be calculated as shown in Equation 9 (using volumetric flow) and Equation 10 (using mass flow for gases).

$$\eta = \kappa \frac{\pi d^2 \Delta P}{4 L \dot{Q}} \quad [9]$$

$$\eta = \kappa \rho \frac{\pi d^2 \Delta P}{4 L \dot{m}} \quad [10]$$

Where:
d=Hydraulic diameter or flow passage diameter of porous restriction or laminar element
A=Hydraulic area or flow passage area
ΔA=Pressure differential across restriction ($P_{upstream}$-$P_{downstream}$)
L=Length over which the pressure drop occurs
η=Fluid absolute viscosity
ρ=fluid density (either gas or liquid)
$M_w$=Molecular weight of the gas
κ=Material permeability (for porous media)
V=volume
t=time
$\dot{Q}$=volumetric flow rate (volume per unit time)
dt=time differential
dV=volume change rate
Z(P,T)=Non-ideal gas compressibility (function of pressure and temp.)

The present invention relates to a method for monitoring a filter installed in a fluid system. The steps include providing a reference region in the fluid system, the region including a chamber having a known volume and releasing a fluid from the chamber configured to flow through the reference region. The method further includes measuring pressure and temperature values at predetermined locations at predetermined time intervals and determining filter permeability values in response to measured pressure and temperature values. The method further includes comparing the filter permeability values to predetermined filter permeability values. The present invention further relates to a method of obtaining a viscosity value for a fluid in a fluid system. The method includes providing a reference region in the fluid system, the region including a chamber having a known volume and releasing a fluid from the chamber configured to flow through the reference region. The method further includes measuring pressure and temperature values at predetermined locations at predetermined time intervals and determining a difference in pressure values at each of the chamber and the reference region at predetermined time intervals. The method further includes determining a filter permeability value from the measured pressure and temperature values and the calculated difference in pressure values and determining at least one of a mass flow rate and a volumetric flow rate of the fluid from at least one of the measured pressure and temperature values and the calculated difference in pressure values, and from a separate device. The method further includes determining a fluid viscosity value, wherein the filter permeability value remains substantially unchanged between the predetermined time intervals.

The present invention further relates to a method of obtaining a viscosity value for a fluid in a fluid system. The method includes providing a reference region in the fluid system, the region including a chamber having a known volume and releasing a fluid from the chamber configured to flow through the reference region. The method further includes measuring pressure and temperature values at predetermined locations at predetermined time intervals and determining a difference in pressure values at each of the chamber and the reference region at predetermined time intervals. The method further includes determining a filter permeability value from the measured pressure and temperature values and the calculated difference in pressure values. The method further includes determining at least one of a mass flow rate and a volumetric flow rate of the fluid from at least one of the measured pressure and temperature values and the calculated difference in pressure values, and from a separate device. The method further includes determining a fluid viscosity value, wherein the filter permeability value remains substantially unchanged between the predetermined time intervals.

The present invention still further relates to a fluid system. The fluid system includes a reference region including a chamber having a known volume and a filter. The fluid system includes pressure and temperature sensors disposed at predetermined locations along the reference region. Upon selective release of a fluid from the chamber configured to flow through the reference region and measurement of pressure and temperature values by the pressure and temperature sensors at predetermined time intervals, filter permeability values are calculable.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

FIGS. 2-3 are schematic views of alternate embodiments of a portion of a fluid system of the present disclosure.

FIG. 4 is a graphical representation of a filter life cycle of the present disclosure.

Wherever possible, the same reference numbers will be used throughout the drawings to refer to the same or like parts.

DETAILED DESCRIPTION OF THE INVENTION

Figure 1:
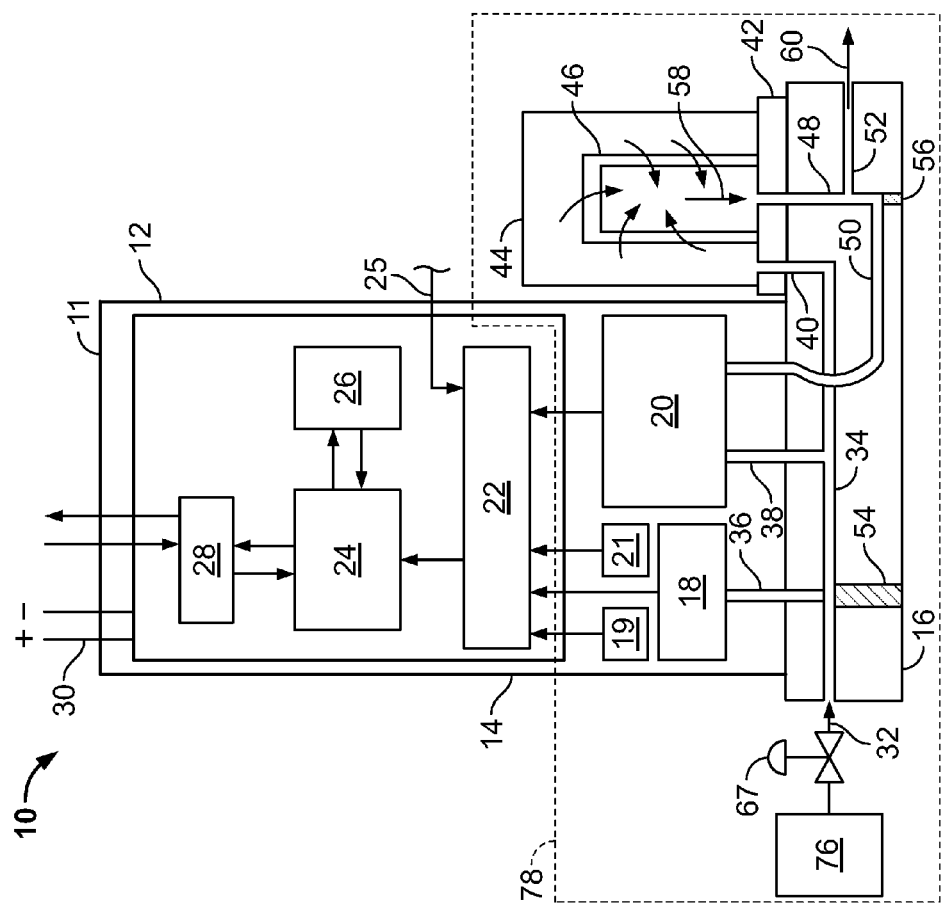
FIG. 1 is a schematic view of an embodiment of a portion of a fluid system of the present disclosure.

Referring now to the drawings, FIG. 1 shows a schematic view of a portion of a fluid system 10, such as for use in fluid flow metering or flow control device 11. Flow control device 11 includes a housing 14 containing various measuring components and a control panel 12, although the measuring components may be exterior of housing 14. Measuring components include, but are not limited to temperature sensors 19, 21 and pressure sensors 18, 20, and may also include mass sensors (not shown) or sensors to measure other fluid parameters. In one embodiment, flow control device 11 is secured to a manifold 16 to which is also secured a filter housing 44 and a manifold 42 for filtering pressurized fluid flow through flow control device 11.

In one embodiment, pressure and/or temperature sensors may be combined into a single device.

As used herein, the term "measuring pressure" in the context of measuring pressure at each of two locations, is intended to include a pressure measurement at a first location and a differential pressure measurement between the first and second locations.

As further shown in FIG. 1, a pressurized fluid 32 from a pressurized fluid source, such as a chamber 76 of known volume, is directed through a passageway 34 formed in manifold 16 upon the opening of a valve 67. Pressure sensor 18 is immediately adjacent to and in fluid communication with pressurized fluid 32 via passageway 36 bridging passageway 34 and sensor 18. Similarly, one leg of differential pressure sensor 20 is in fluid communication with pressurized fluid 32 via passageway 38 bridging passageway 34 and pressure sensor 20. In one embodiment, a bypass outlet 54 is in fluid communication with passageway 34 to further direct pressurized fluid 32, if desired. Pressurized fluid 32 is further directed through passageway 34 and then passageway 40 before flowing into filter housing 44 and then through filter element or filter 46 to remove particulates entrained in pressurized fluid 32.

After passing through filter 46, pressurized fluid 32 becomes filtered fluid 58. Upon passing through filter 46, filtered fluid 58 is then directed through passageway 48. The other leg of differential pressure sensor 20 is in fluid communication with filtered fluid 58 via passageway 50 bridging passageway 48 and differential pressure sensor 20 so that differential pressure sensor 20 measures the difference in pressure between pressurized fluid 32 and filtered fluid 58. In one embodiment, a bypass outlet 56 is in fluid communication with passageway 48 to further direct filtered fluid 58, if desired. Filtered fluid 58 is further directed through passageway 52 in fluid communication with passageway 48, which fluid referred to as pressurized fluid 60. For ease of description and convenience, the pressure value or magnitude as sensed by pressure sensor 18 is referred to as P1 and the pressure value or magnitude as sensed by the one leg of pressure sensor 20 in communication with passageway 50, which is pressurized fluid 60, is P2. The pressure value P2 refers to the backpressure downstream in fluid system 10. It is to be understood that while pressurized fluid 32 (P1) is shown in FIG. 1 upstream of filter 46 and pressurized fluid 60 (P2), and that the pressure value or magnitude of pressurized fluid 32 (P1) is greater than the pressure value or magnitude of pressurized fluid 60 (P2), both the pressure magnitudes and thus, directions of travel of the pressurized fluids, may be reversed.

As further shown in FIG. 1, flow control device 11 operates as follows. After valve 67 is opened, pressure values or magnitudes of pressurized fluid 32 (P1) from chamber 76 are sensed or measured by pressure sensor 18 at predetermined time intervals, while differential pressure values or magnitudes between pressurized fluid 32 (P1) and pressurized fluid 60 (P2) are substantially simultaneously sensed or measured.

For convenience, this differential pressure corresponding to locations of pressurized fluids 32, 60 disposed on opposite sides of filter 46 is referred to in FIGS. 5-9 as ΔP. Similarly, temperature values corresponding to positions in close proximity of pressurized fluids 32 (P1), 60 (P2), if required, are sensed or measured by temperature sensors 19, 21 (T1, T2) at predetermined time intervals substantially simultaneously as the pressurized fluid measurements.

Once the temperature/pressure measurements are performed, the pressure sensors 18, 20 and temperature sensors 19, 21 transmit signals corresponding to those measurements to an amplifier/converter 22 to amplify and/or convert the signals from analog to digital form, if required. In one embodiment, signals 25 from other devices (not shown) permitting mass flow measurement, such as precision mass measurement devices or a mass spectrometer, may be transmitted to amplifier/converter 22 to amplify and/or convert the signals 25 from analog to digital form, if required.

After the various signals, e.g., P1, ΔP, T1, T2, are transmitted from amplifier/converter 22 to microprocessor 24, and saved in a storage device 26, such as an EEPROM, various calculations are performed as is known in the art, such as volumetric fluid flow from chamber 76 over time versus differential pressure, for example by application of Equation 7 to yield a filter permeability constant (e.g., see $K_i$ of FIG. 4). Once the filter permeability constant value K is calculated, it may be stored and/or compared to previously stored filter permeability constant values in storage device 26. In one embodiment, a time reference corresponding to each calculated filter permeability constant value K is saved and compared in order to determine when subsequent filter permeability calculations should be performed, based on historical data. That is, over time, filter permeability values K, i.e., the slopes of the curves shown in FIG. 4, decrease. FIG. 4, which is a graphical representation of the life cycle of a filter, further shows an operational region 72 and a "replacement recommended" region 74. For example, filter permeability curve $K_i$ corresponds to an initial filter permeability curve, such as when the filter is new and substantially unclogged or uncontaminated with particulates. A significant portion of the filter permeability curve $K_i$ is contained in the operational region 72 of FIG. 4. However, a significant portion of the filter permeability curve K3 i.e., the third calibration of the filter, is contained in the replacement recommended region 74, and is near the end of its operating life. Due to the accumulation of data in storage device 26, trends relating to filter life are identified, seeking a balance between minimizing the number of filter monitoring cycles, which can result in shut-down of portions of fluid system 10, and probability of operating filters in a replacement recommended region 74, or filter failure.

It is appreciated that electrical power required to operate components of flow control device may be provided by an electrical power source 30, which includes, but is not limited to, a power grid, batteries or other sources. Additionally, in one embodiment, a transceiver 28 may receive and exchange information such as from a digital bus, which may be transmitted over power lines or other wired or wireless devices and/or techniques.

In order to minimize or eliminate shut-down of a portion of fluid system 10 while a filter 46 is being replaced, flow control device 11 may include multiple modules 78 (only one shown in FIG. 1). In one embodiment, multiple modules 78 are disposed in a parallel flow arrangement, such that one module 78 may be maintained in fluid communication with the fluid system 10 while the other modules 78 are selectably isolated, such as by use of valving arrangements (not shown) to replace filters 46 or to perform a filter monitoring cycle without disturbing operation of the fluid system. In one embodiment, module 78 includes a filter housing 44 (and filter 46), manifolds 16, 42 and corresponding sensors 18, 19, 20, 21, although the sensors may have multiple leads, with the leads corresponding to the operating module remaining on-line being active. Therefore, in another embodiment of module 78, the only components include a filter housing 44 (and filter 46), associated manifolds 16, 42 and sensor leads.

Figure 2:
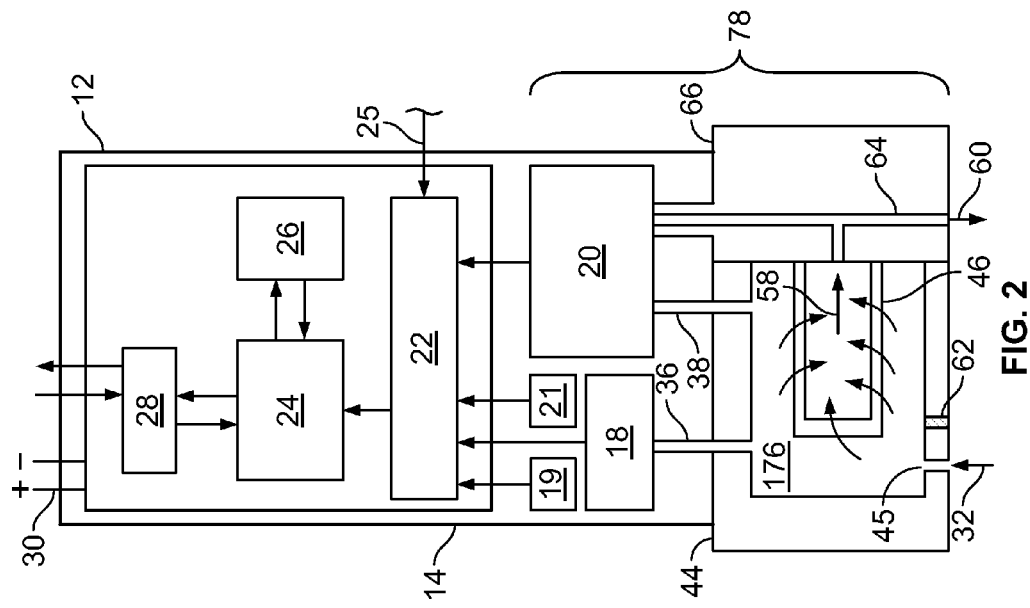

As shown in FIG. 2, which is otherwise similar to FIG. 1, filter housing 44 abuts and is in fluid communication with pressure sensors 18, 20. As a result, manifolds 16, 42 from FIG. 1 are not required. A removable cap 66 abuts filter housing 44 and filter 46 and is in fluid communication with both filter 46 and one leg of differential pressure sensor 20 by virtue of tee passageway 64. Upon removal of cap 66, filter 46 can be replaced. Pressurized fluid 32 (P1) is provided directly into filter housing 44, the volume between filter 46 and the inner surfaces of filter housing 44 defining a chamber 176 being a known volume in one embodiment. An optional bypass 62 can be used to evacuate pressurized fluid 32 in fluid housing 44.

It is to be understood that the filter permeability K decreases over time in response to becoming gradually more clogged, and must therefore be monitored, as the equations must account for the change in filter permeability to provide accurate information.

FIG. 3 shows the arrangement of FIG. 2 with a valve 68 disposed upstream of opening 45 and a valve 70 disposed downstream of cap 66 and there being a known volume between filter 46 and the inner surfaces of filter housing 44 (chamber 76).

The following steps are followed to monitor or re-calibrate the filter permeability K as follows.

1) Valve 68 is opened and valve 70 is closed, until a maximum, stable pressure value is achieved therebetween.
2) Valve 68 is closed and valve 70 opened, permitting pressurized fluid in chamber 176 to become filtered fluid 58 flowing through filter 46 until the differential pressure measured by differential pressure sensor 20 is substantially zero. At predetermined time intervals, pressure values as measured by pressure sensor 18 and differential pressure sensor 20 are stored in storage device 26.
3) The rate at which the volume of chamber 176 is depressurized can be measured by virtue of the multiple pressure sensor 18 readings taken at predetermined time intervals. By dividing the volume of chamber 176 by the time of depressurization, yields average volumetric flow rate, Equation 2 can be calculated.
4) The average volume flow rate is dividing by the average change in pressure over time to yield a new filter permeability value (K), which is stored in storage device 26.
5) Valves 68, 70 are reopened, with the flow control device returning to measuring flow and with multiple pressure readings taken at predetermined time intervals across the filter, checking for anomalies, as will be discussed in conjunction with FIGS. 5-9 below, and for trending data.

It is to be understood that in one embodiment of flow control device 11 where the filter 46 is not substantially contaminated or clogged and fluid viscosity is sufficiently low, such as less than about 100 centipoise and exhibiting Newtonian behavior, i.e., substantially devoid of shear thinning or thickening, the flow control device 11 can obtain an inferential value of the viscosity of the fluid.

FIG. 3 shows the arrangement of FIG. 2 with a valve 68 disposed upstream of opening 45 and a valve 70 disposed downstream of cap 66 and there being a known volume between filter 46 and the inner surfaces of filter housing 44 (chamber 76). The following steps are followed to measure fluid viscosity η.

1) Valve 68 is opened and valve 70 is closed, until a maximum, stable pressure value is achieved therebetween.
2) Valve 68 is closed and valve 70 opened, permitting pressurized fluid in chamber 176 to become filtered fluid 58 flowing through filter 46 until the differential pressure measured by differential pressure sensor 20 is substantially zero. At predetermined time intervals, pressure values as measured by pressure sensor 18 and differential pressure sensor 20 are stored in storage device 26.
3) The rate at which the volume of chamber 176 is depressurized can be quantified by virtue of the multiple pressure sensor 18 readings taken at predetermined time intervals. Dividing the volume of chamber 176 by the time of depressurization yields average volumetric flow rate $\dot{Q}$.
4) The average volume flow rate is then divided by the average change in pressure over time to yield a new filter permeability value K, which is stored in storage device 26.

Since filter permeability K is originally calculated with a known fluid, deviation of differential pressure ΔP may be an indication of a change in fluid viscosity η. If filter permeability K is assumed to be substantially constant, repeating numbered steps 1)-3) above can be used to calculate fluid viscosity η, versus filter permeability K.

Figure 5:
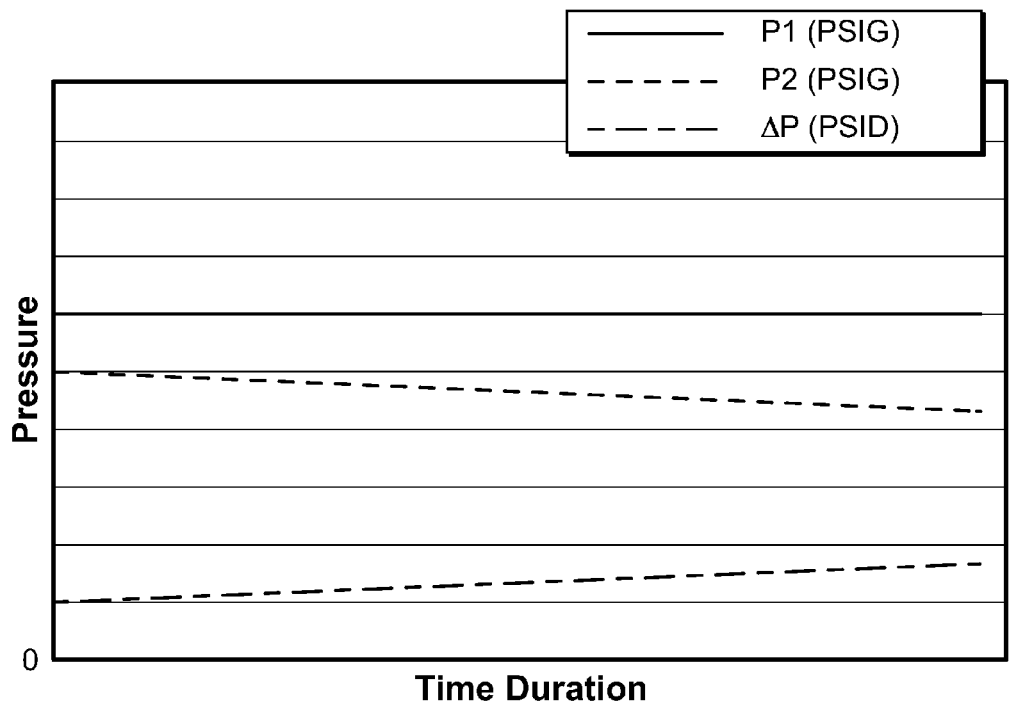
FIGS. 5-10 are graphical representations of different operating scenarios encountered by a fluid system of the present disclosure.

FIGS. 5-9 correspond to various scenarios flow control device 11 can encounter during operation. For example, as shown in FIG. 5, P1 stays substantially constant, but ΔP increases and backpressure P2 decreases. In response, a possible action is to obtain backpressure from another sensor monitoring P2, if possible. If P2 continues to decrease below a predetermined critical level, the control panel notifies the operator, such as by a low backpressure message. For example, this scenario may be indicative of a process upset on the return line, a leak in the fluid system, or some other fluid system upset.

Figure 6:
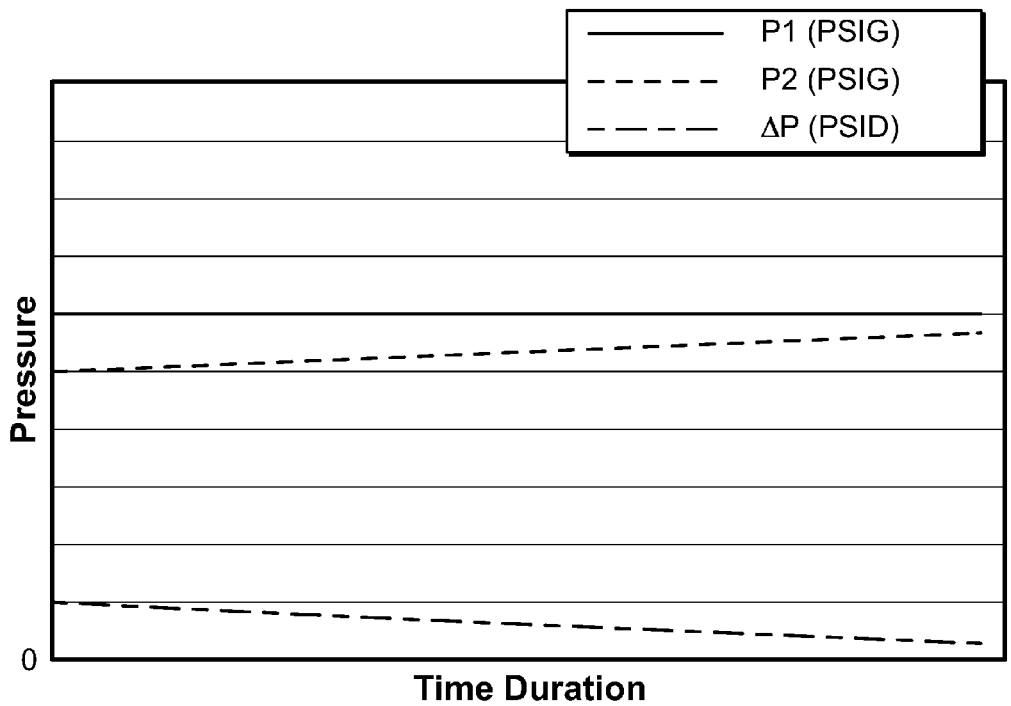

As shown in FIG. 6, P1 stays substantially constant, but ΔP decreases and backpressure P2 increases. In response, a possible action is to obtain backpressure from another sensor monitoring P2, if possible. If P2 continues to increase above a predetermined critical level, the control panel notifies the operator, such as by a low backpressure message. For example, this scenario may be indicative of a clogged sample return line for bypass filters or a clogged/malfunctioning device/passage downstream.

Figure 7:
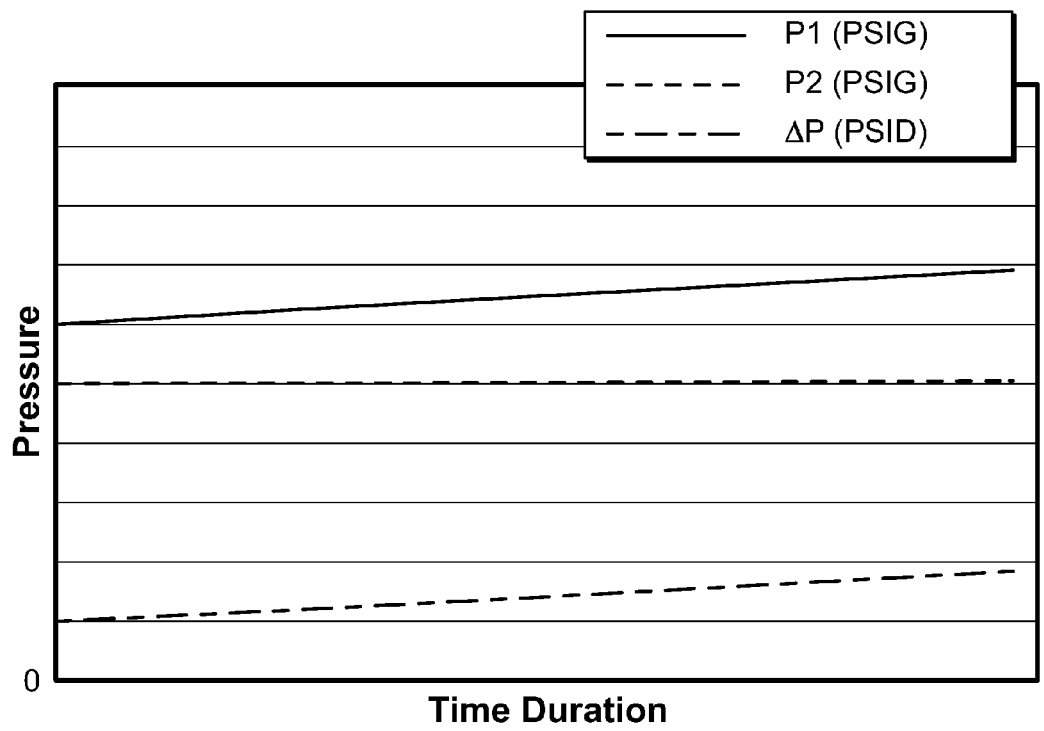

As shown in FIG. 7, P1 increases, but P2 remains substantially constant and ΔP backpressure increases. It is then assumed that the filter permeability K has decreased, i.e., the filter is clogging. In response, once calculated filter permeability decreases past a predetermined amount, the control panel notifies the operator, such as with a filter replacement message.

Figure 8:
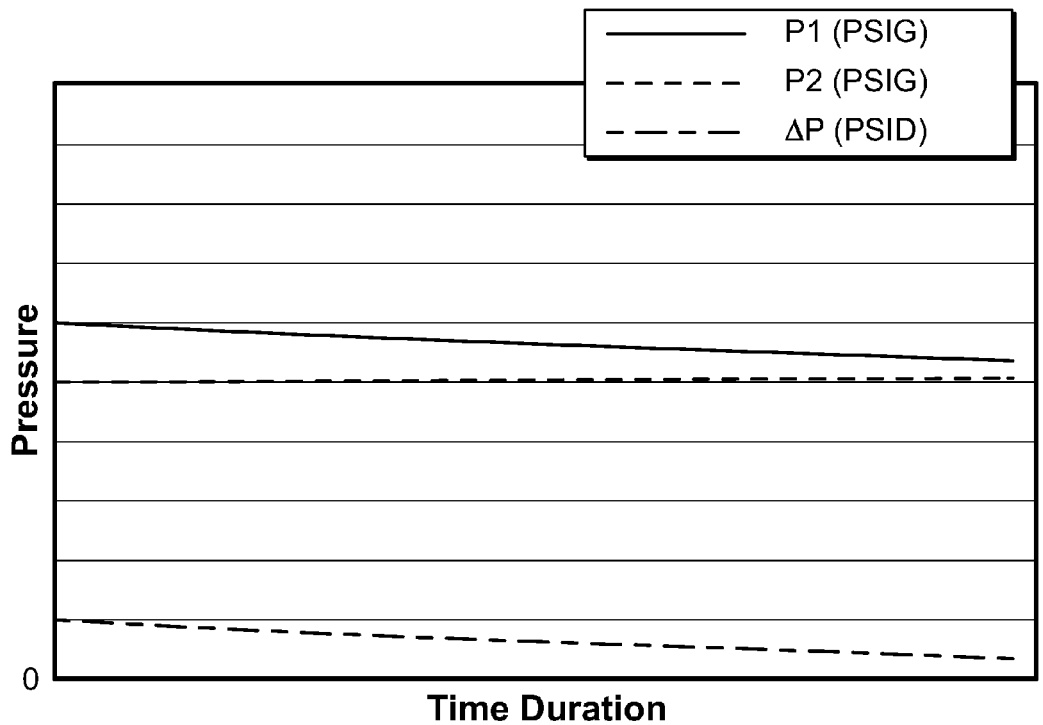

As shown in FIG. 8, P1 decreases, but P2 remains substantially the same and ΔP backpressure decreases. It is then assumed that there is a low flow condition or obstruction upstream of the filter or a system leak. In response to a sufficient ΔP backpressure decrease in combination with P1 decrease, the control panel notifies the operator, such as with a low flow condition message.

Figure 9:
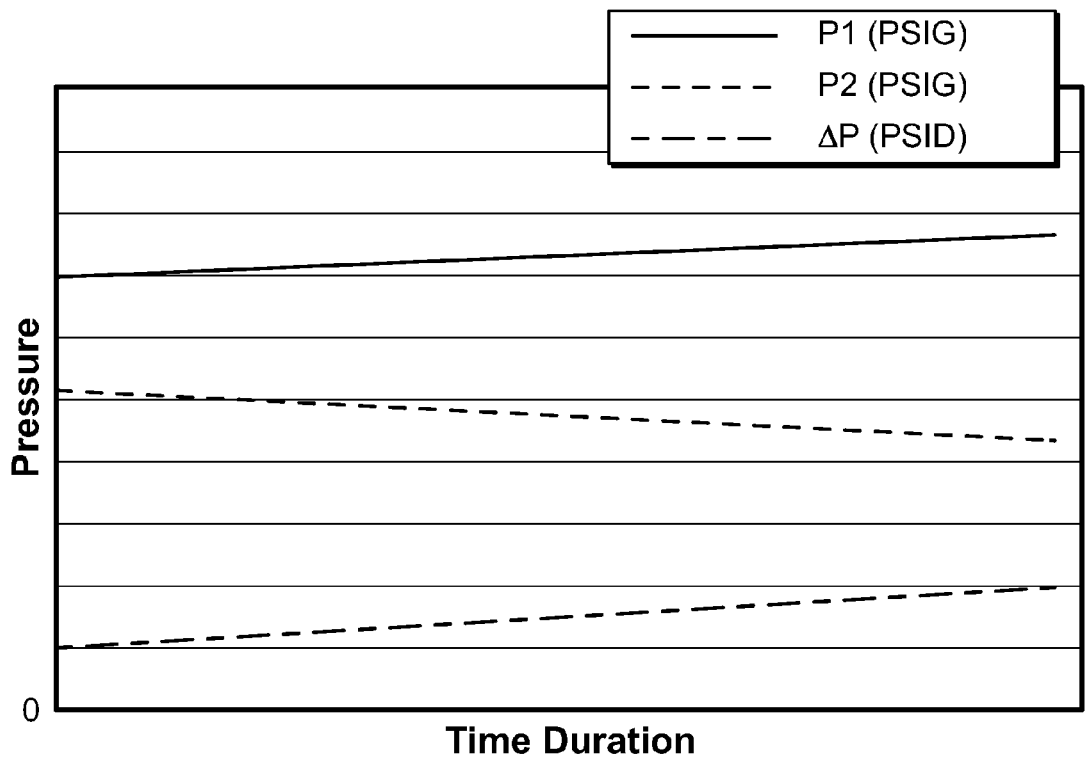

As shown in FIG. 9, P1 increases, but P2 decreases and ΔP backpressure increases. It is then assumed that there are pressure regulation creep problems, or filter clogging with a simultaneous decrease in outlet pressure. In response to a sufficient ΔP backpressure increase in combination with P1 increase and P2 decrease, the control panel notifies the operator, such as with a general system error message.

Figure 10:
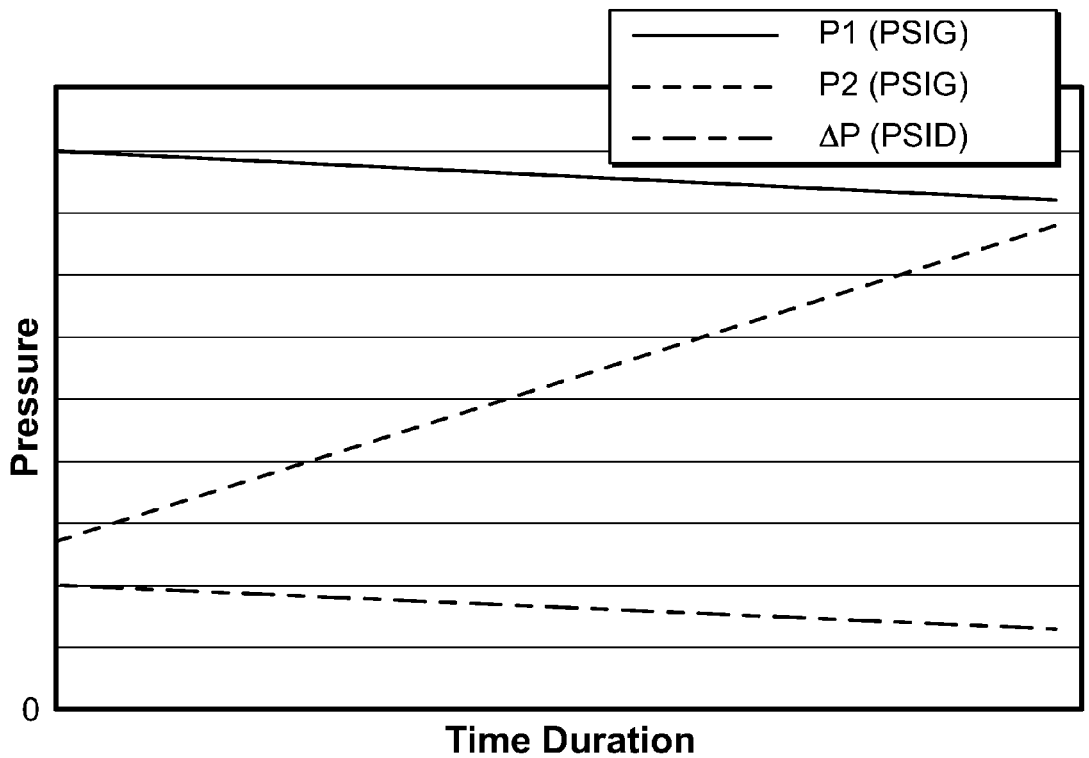

As shown in FIG. 10, P1 decreases, P2 increases and ΔP backpressure increases. This scenario could mean that a valve or restriction upstream caused interruption in inlet flow and a backflow condition in the system. This condition would normally be transient, as P1 and P2 would equalize and ΔP would equilibrate, unless a sufficient amount of particulate clogged the valve from the backside and effectively plugged the filter thereby allowing backpressure to remain higher than inlet pressure. In response to this condition, the control panel notifies the operator, such as with a general system error message.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for monitoring a filter installed in a fluid system, the steps comprising:
   providing a continuous pressurized fluid source; providing a fixed reference region in the fluid system, the region including a chamber having a known volume;
   releasing a fluid from the chamber configured to flow through the reference region and a filter;
   measuring varying pressure and temperature values at predetermined locations at predetermined time intervals;
   measuring mass or volumetric flow rate based on the time of depressurization of the chamber of known volume;
   calculating filter permeability values in response to dynamic changes in measured pressure and temperature values; and
   comparing the filter permeability values to predetermined filter permeability values;
   wherein the pressurized fluid source is in continuous fluid connection with the predetermined locations while the pressure and temperature values are being measured and while the filter permeability values are being calculated and compared.

2. The method of claim 1, further including an additional step after the comparing step of storing the filter permeability values.

3. The method of claim 2, further including an additional step after the comparing step, in which a previous and most recently stored permeability value is replaced by the current calculated permeability value.

4. The method of claim 2, wherein the storing step further includes a time signature pertaining to the date and time at which a particular filter permeability value was calculated.

5. The method of claim 4, further including an additional step after the storing step of indicating an estimated time duration corresponding to a filter replacement based on previously stored filter permeability values.

6. The method of claim 4, further including an additional step after the storing step of indicating an estimated time duration for a subsequent monitoring of the filter based on previously stored filter permeability values.

7. The method of claim 1, wherein the chamber is upstream of the filter.

8. The method of claim 1, wherein the chamber is immediately adjacent to the filter.

9. The method of claim 1, further including an additional step after the comparing step of replacing the filter in response to the filter permeability values being less than predetermined filter permeability values.

10. The method of claim 9, wherein the replacing step is performed without having to interrupt operation of the fluid system.

11. The method of claim 10, wherein the replacing step is conducted in parallel with the fluid system.

\* \* \* \* \*

UNITED STATES PATENT AND TRADEMARK OFFICE
CERTIFICATE OF CORRECTION

| | | |
|---|---|---|
| PATENT NO. | : 7,937,987 B2 | Page 1 of 1 |
| APPLICATION NO. | : 11/864133 | |
| DATED | : May 10, 2011 | |
| INVENTOR(S) | : Lowery | |

It is certified that error appears in the above-identified patent and that said Letters Patent is hereby corrected as shown below:

Column 2, line 38, "$\Delta A$=Pressure differential across..." should read --$\Delta P$=Pressure differential across...--

Signed and Sealed this
Twenty-eighth Day of June, 2011

David J. Kappos
*Director of the United States Patent and Trademark Office*